United States Patent [19]
Mikhail

[11] Patent Number: 5,303,694
[45] Date of Patent: Apr. 19, 1994

[54] METHOD FOR PERFORMING HIP SURGERY AND RETRACTOR FOR USE THEREIN

[76] Inventor: W. E. Michael Mikhail, 4203 Shamley Green, Toledo, Ohio 43623

[21] Appl. No.: 15,548
[22] Filed: Feb. 9, 1993
[51] Int. Cl.⁵ ............................................. A61B 17/02
[52] U.S. Cl. ..................... 128/20; 606/205; 606/208
[58] Field of Search .................. 128/20, 17, 3, 4; 606/151, 205, 208, 96

[56] References Cited

U.S. PATENT DOCUMENTS

| | | |
|---|---|---|
| 2,695,607 | 11/1954 | Hipps et al. . |
| 3,731,673 | 5/1973 | Halloran . |
| 3,750,652 | 8/1973 | Sherwin ........................ 128/17 |
| 3,801,989 | 4/1974 | McKee . |
| 3,955,568 | 5/1976 | Neufeld . |
| 4,190,042 | 2/1980 | Sinnreich . |
| 4,355,631 | 10/1982 | LeVahn . |
| 4,686,972 | 8/1987 | Kurland . |
| 4,726,356 | 2/1988 | Santilli et al. . |
| 4,747,395 | 5/1988 | Brief . |
| 5,052,373 | 10/1991 | Michelson ..................... 128/20 |

FOREIGN PATENT DOCUMENTS 1487486 of 0000 France .
1274432 of 0000 United Kingdom .

OTHER PUBLICATIONS

Stille (1939) Catalog of Stainless Steel Retractors.
D. H. Levinthal, Jornal of Bone & Joint Surgery (1931) "Knee Joint Retractors For Resections and Arthroplasties", pp. 378, 379.
Zimmer Inc. Catalog (1966), pp. 116, 117 and A163.

Primary Examiner—Richard J. Apley
Assistant Examiner—Beverly A. Meindl
Attorney, Agent, or Firm—Emch, Schaffer, Schaub & Porcello Co.

[57] ABSTRACT

A surgical retractor for use in performing hip surgery includes a pair of wing members mounted on a hinge pin for pivotal movement thereabout relative to one another. The hinge pin has one end mounted on a handle and carries a guide member at its opposing end. In performing surgery, the surgeon inserts the retractor, guide member first, with the wing members in a folded position, anchors the hinge pin in place by means of a nail driven into the bone and then opens the wing members to expose the hip socket for surgery. The wing members have guides which receive retention pins driven into the bone to retain the wing members in the desired open position.

35 Claims, 5 Drawing Sheets

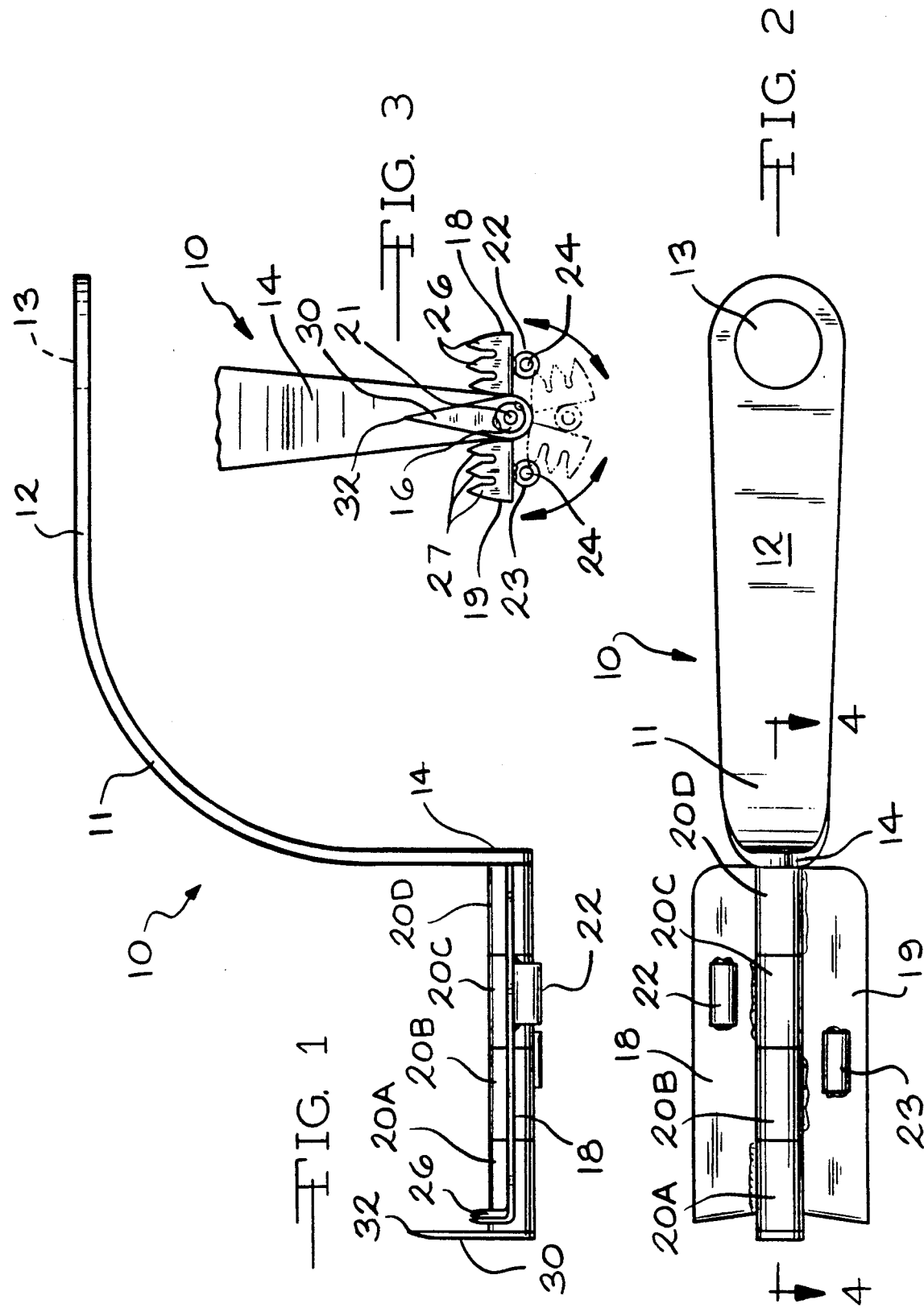

METHOD FOR PERFORMING HIP SURGERY AND RETRACTOR FOR USE THEREIN

BACKGROUND ART

In performing hip surgery it is of the utmost importance to avoid or at least minimize damage to ligaments, tendons, muscles, nerves and other portions of the soft tissue while gaining access to and performing surgical procedures on various portions of bone structure of the hip. Surgical retractors of various forms and shapes have long been used to assist the surgeon in obtaining access to the surgical site by opening the incision and/or retracting those parts of the soft tissue.

U.S. Pat. No. 4,686,972 discloses a combination surgical deflector and drilling guide designed for uncovering the bone to be worked upon with the retractor equipped with a positioner which firmly positions the retractor on the bone and provides a guide for the drill or other medical instruments to be used during surgery.

U.S. Pat. No. 3,955,568 discloses a tool for inserting a prosthetic femoral head into and for removing it from a prosthetic hip socket.

U.S. Pat. No. 3,731,673 is directed to a self-retaining muscle retractor which eliminates the necessity of stripping the bone around its entire periphery thus enabling its use in the hip area and other areas where the underside of the bone cannot be readily stripped. It has a pair of elongated retractor members with bone-engaging portions at their lower ends and having their upper extremities defining lever arms. A brace is pivotally connected on one end to the upper extremity of one of the lever arms and has its free end engagable with latching elements on the other lever arm whereby the bone-engaging portions may be inserted in an incision, engaged on opposite sides of a bone, the lever arms spaced apart and the free end of the brace engaged with a latching element to maintain the incision open.

None of the prior art, however, is specifically designed to provide means for gaining access to and retracting the soft tissue from the hip joint while at the same time providing means for inserting, positioning, opening and anchoring such retractor in position while the surgeon performs surgical procedures.

DISCLOSURE OF THE INVENTION

The present invention is directed to a surgical retractor and a method for performing surgery using such retractor. The retractor of the present invention is provided with a pair of hinged wings positioned on opposite sides of a guide which is inserted into the incised area to locate the appropriate positioning for exposure. During insertion, the wings are in a folded position. The wings are provided with fingers which grip beneath the muscle to retract it without causing undue damage to the muscle fiber. When properly positioned, the retractor is pinned or otherwise firmly secured in position and the wings are then moved to an open position and are themselves anchored by means of a pin affixed to the bone.

BRIEF DESCRIPTION OF THE DRAWINGS

FIG. 1 is an elevational view of the retractor of the present invention.

FIG. 2 is a bottom view of the retractor shown in FIG. 1.

FIG. 3 is a fragmentary end view of the retractor taken from the left end of FIG. 1.

BEST MODE OF CARRYING OUT INVENTION

Figure 4:
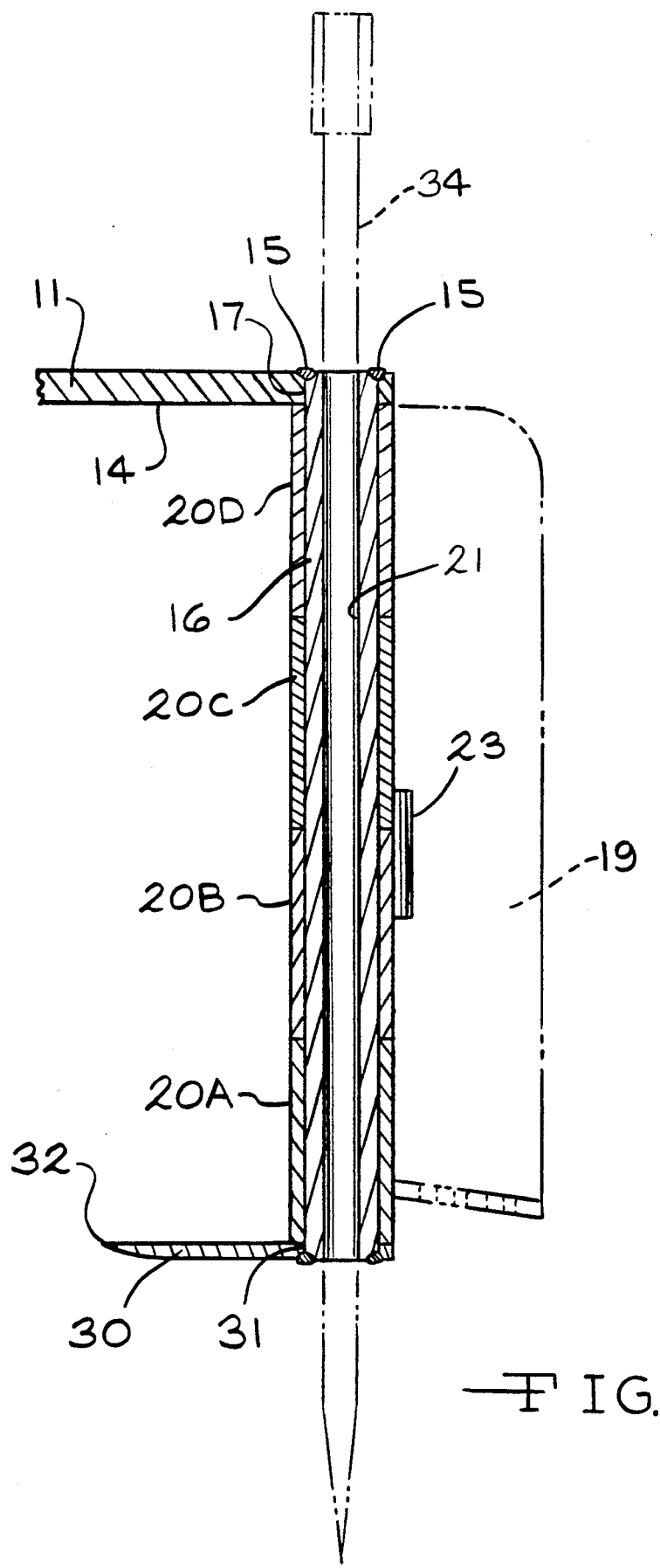
FIG. 4 is a sectional view taken through line 4—4 of FIG. 2.

Referring now to FIGS. 1-4, there is provided a retractor 10 having a curved handle 11 with a gripping end 12 which is substantially planar and lying in a first plane. If desired, the gripping end may be provided with an aperture 13 into which a weighted hook may be placed to temporarily retain the retractor in position prior to its being anchored in position. Beginning approximately midway of its length, the handle becomes curved and follows a curved path merging into an attachment end 14 which follows a planar path positioned substantially at right angles to the plane of the gripping end 12.

Extending outwardly from and rigidly secured to the attachment end 14 of the handle 11 is a tubular hinge pin or pivot 16 having a passageway 21 extending therethrough. Preferably, the hinge pin/pivot 16 is disposed at right angles to the attachment end 14 and is substantially parallel to the gripping end 12. The hinge pin/pivot 16 is received in an aperture 17 formed in the attachment end 14 and is retained therein by means of welds 15. A pair of wing members 18 and 19 are pivotally mounted on the hinge pin/pivot 16 by means of four bushings 20A, 20B, 20C and 20D mounted on the hinge pin/pivot 16 for rotational movement relative thereto. The first wing member 18 is welded or otherwise permanently mounted on bushings 20A and 20C and the second wing member 19 is permanently mounted on the other two bushings 20B and 20D. Thus, the wing members 18 and 19 are free to rotate relative to one another as well as rotate relative to the handle 11.

Each of the wing members 18 and 19 has welded or otherwise permanently adhered thereto a tubular pin guide, one identified by the numeral 22 for the wing member 18 and the other by the numeral 23 for the wing member 19. The pin guide 22 is positioned closer to the handle 11 than the pin guide 23 in order than the wing members 18 and 19 may be folded toward one another in a downward direction as shown in phantom in FIG. 3 without interfering with one another. The pin guides 22 and 23 are tubular and each has a passageway 24 for receiving a pin therethrough.

The ends of each of the wing members 18 and 19 furtherest removed from the handle 11 are bent at 90° to form flanges each of which has a plurality of three fingers extending therefrom. The fingers are identified by the numeral 26 for fingers extending from the flange of the wing member 18 and by the numeral 27 for fingers extending from the flange of the wing member 19.

Rigidly mounted on the end of the hinge pin/pivot 16 is a clip or guide member 30. The clip/guide member 30 is provided with an aperture 31 at the end engaged to the hinge pin/pivot 16 and extends along a taper to a pointed tip 32. As can be seen in FIGS. 1 and 4, the clip/guide member 30 is also tapered throughout its thickness to the tip 32. The clip/guide member 30 is welded or otherwise permanently affixed to the hinge pin/pivot 16 in order that it can be guided by the surgeon during the procedure of insertion into the desired site for surgery.

Figure 5:
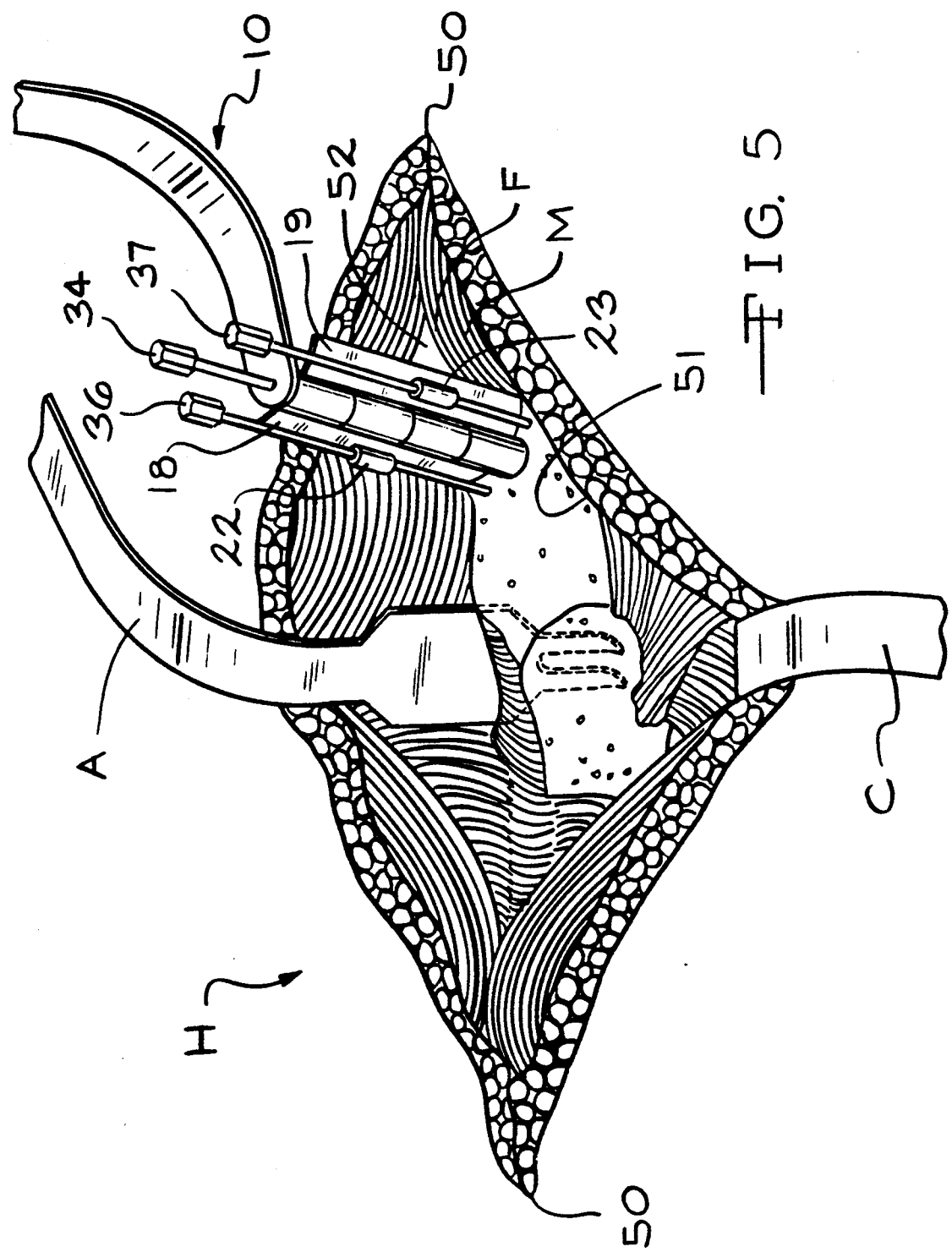
FIGS. 5, 6 and 7 are a perspective views showing the retractor of the present invention in use during surgery.
Figure 6:
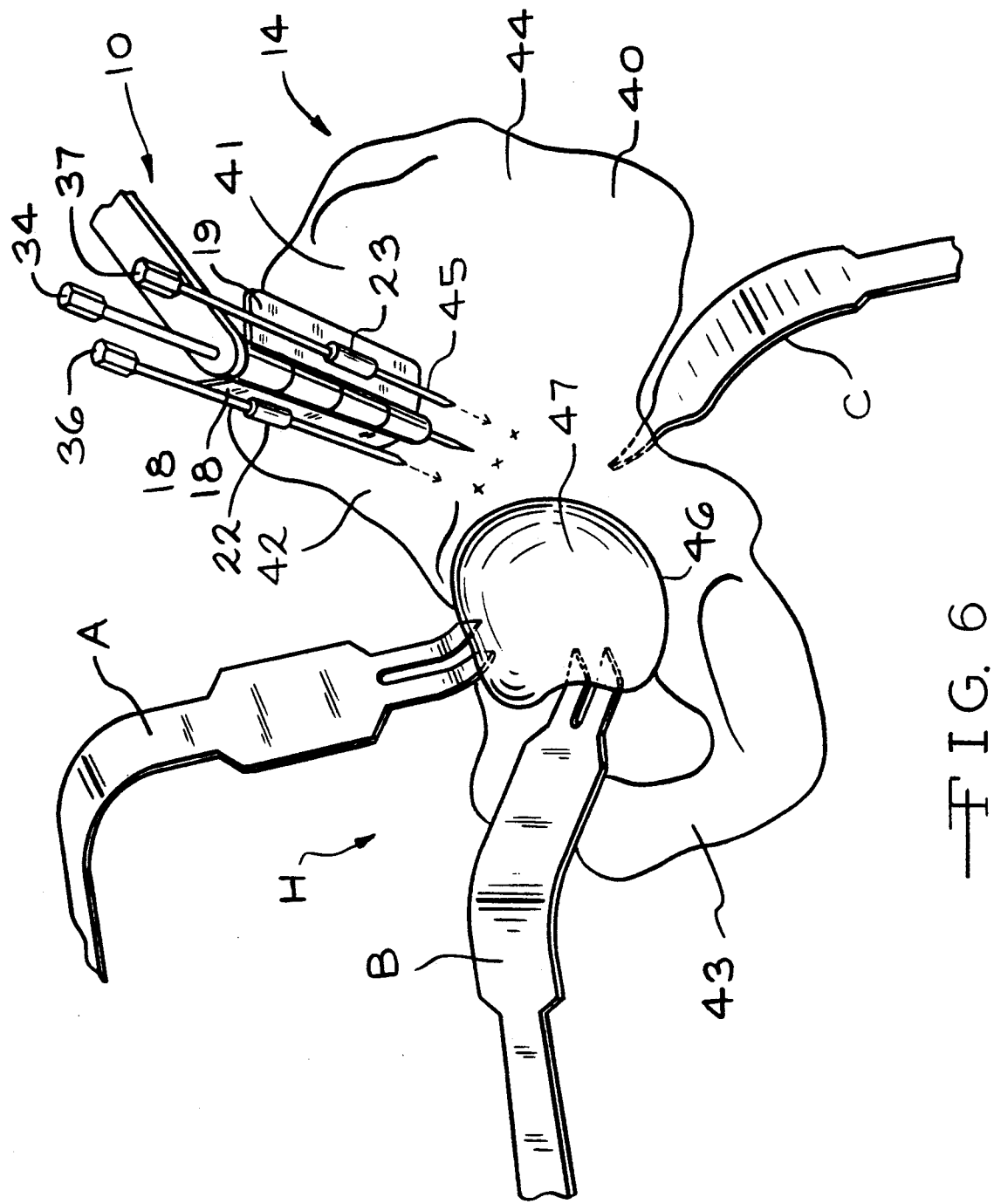
Figure 7:
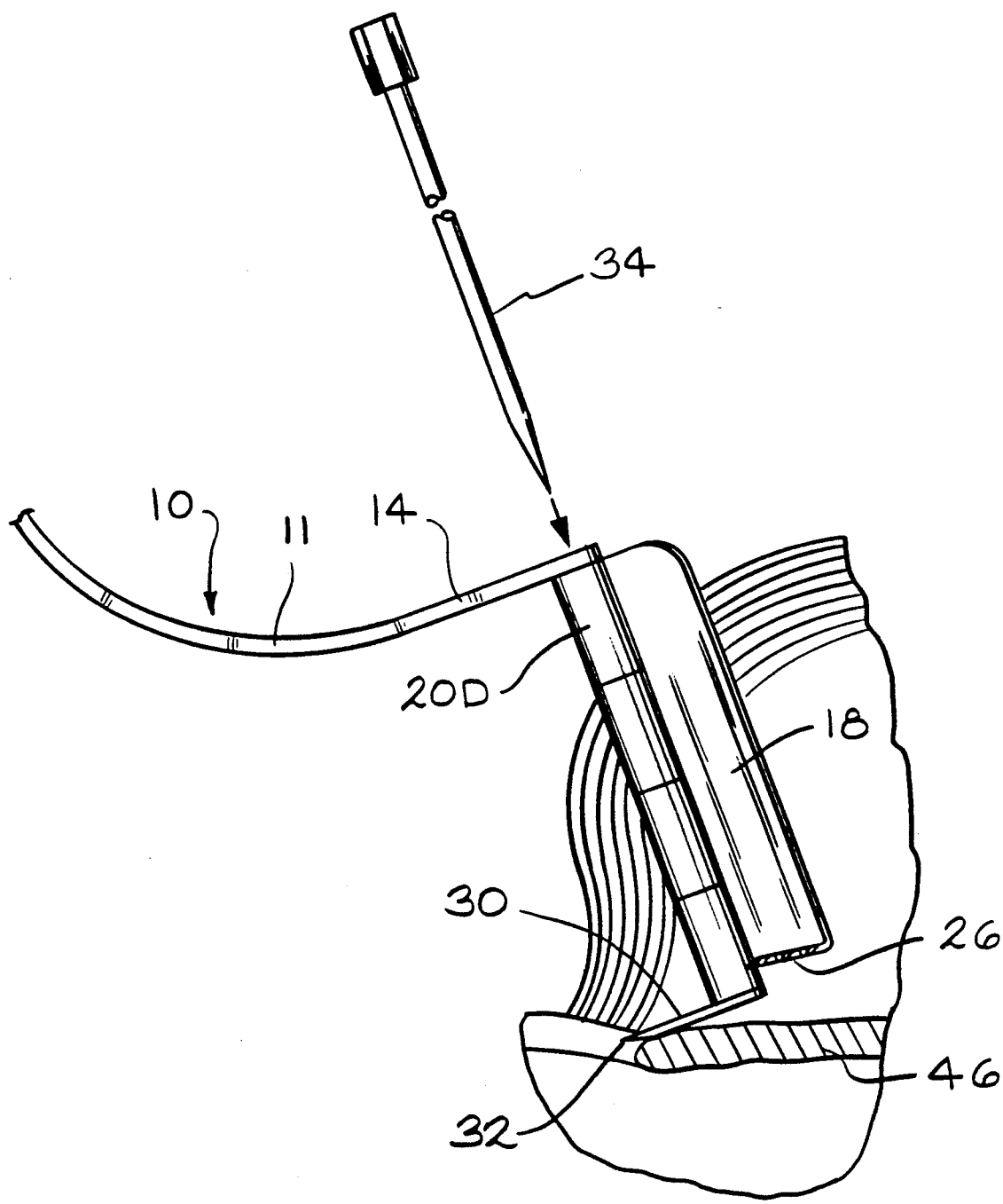

Referring now to FIGS. 5, 6 and 7, there will now be described the method of using the retractor 10 according to the method of the present invention. There is shown a fragmentary portion of a hip H of a patient undergoing surgery. Shown in FIG. 6 is the posterior portion 40 at the lower right, the superior portion 41 at the upper right, the anterior portion 42 at the upper center and the inferior portion 43 at the left. The iliac wing 44 is generally between the posterior portion 40 and the superior portion 41. As shown in FIG. 6, the retractor 10 is to be positioned in the supra-acetabular margin 45 in order to expose the hip joint 46 including the socket 47. As will be appreciated and as can be seen in FIGS. 5 and 6, other various retractors A, B and C are used to retract other portions of the soft tissue.

Prior to use of the retractor 10 of the present invention, the surgeon will make a first incision 50 in the skin overlying the patient's hip generally in line with the patient's leg. He will then make a second incision 51 of the fascia lata in line with the first incision 50. Thereafter, in accordance with the present invention, the surgeon will make an incision 52 of the minimos muscle M in line with its fibers F as illustrated in FIG. 5. Following this, the surgeon will insert the retractor 10 with the tip 32 of the guide member 30 leading the way. During such insertion, the wing members 18 and 19 will be in a folded position such that the pin guide 22 of wing member 18 will contact the wing member 19 and the pin guide 23 of wing member 19 will contact the wing member 18. As will be appreciated, if the pin guides 22 and 23 were aligned with one another, such folding of the wing members 18 and 19 would cause the pin guides 22 and 23 to strike one another and, thus, unnecessarily limit the extent to which the wing members 18 and 19 may be folded. The surgeon carefully moves the guide member 30 snugly on the bone under the periosteum so that it is positioned subperiosterly in order to protect the neurovascular bundle. With the retractor 10 thus positioned, a retention pin 34 is inserted through the passageway 21 of the hinge pin/pivot 16 and is driven into the bone thus fixing the hinge pin/pivot 16 firmly in place. The retention pin 34 is positioned in the supra-acetabular margin of the iliac wing 44.

The wing members 18 and 19 are then opened to an optimal position carrying with them the muscle and other soft tissue engaged thereby. The fingers 26 and 27 are positioned beneath the muscle M which is quite thin in that area. The wing members 18 and 19 may be opened to a position at or approaching 180° from one another. The optimal extent to which the wing members are opened will vary depending upon the particular patient. However, the object is to obtain optimal exposure of the hip joint 46 including the socket 47 through use of the retractor 10 of the present invention.

After the wing members 18 and 19 are opened to the optimal extend, additional retention pins 36 and 37 are inserted respectively in the passageways 24 of pin guides 22 and 23. They are then firmly anchored in the bone preferably by pounding. However, depending upon the condition of the patient, it may be desirable to fix some or all of the retention pins 34, 36 and 37 by initially drilling a receptor passage in the underlying bone. With the retractor 10 thus firmly anchored in position, the surgeon may then proceed with the conventional procedures required for the specific hip surgery involved.

Many modifications to the present application will become readily apparent to those skilled in the art.

I claim:

1. A surgical retractor comprising:
   (a) a handle having a substantially planar end portion defining a first plane, a gripping portion disposed at an angle relative to said first plane and an intermediate portion between said end portion and said gripping portion;
   (b) a hinge supported from said end portion and extending at substantially right angles to said end portion to a free end, said hinge lying in a second plane which is disposed at substantially right angles to said first plane and which extends through said end portion, said intermediate portion and said gripping portion; and
   (c) a pair of wing members mounted on said hinge for pivotal movement thereabout and angular movement relative to one another, each of said wing members having a major portion adjacent said hinge extending from a first end adjacent said handle end portion to a second end adjacent said free end and a plurality of fingers depending from said second end at an angle to said major portion.

2. The surgical retractor of claim 1, wherein said fingers are disposed at substantially right angles to said major portion.

3. The surgical retractor according to claim 1, wherein said hinge has a passageway extending therethrough for receiving a retention pin.

4. The surgical retractor of claim 3 further including means on each of said wing members for receiving a retention pin.

5. The surgical retractor according to claim 1 further including a guide member mounted on said hinge free end.

6. The surgical retractor according to claim 5, wherein said guide member is disposed at substantially right angles to said hinge and tapers from a wide end at said hinge to a narrower free end.

7. The surgical retractor according to claim 6, wherein said guide member extends in a direction reverse to the direction of said handle planar end portion.

8. A surgical retractor comprising:
   (a) a handle having a gripping end and a supporting end disposed at an angle relative thereto;
   (b) a hinge supported from said supporting end and extending to a free end, each of said hinge, said gripping end and said supporting end being generally aligned in a common plane;
   (c) a pair of wing members mounted on said hinge for pivotal movement thereabout and angular movement relative to one another.

9. A surgical retractor according to claim 8, wherein said hinge has a passageway extending therethrough for receiving a retention pin.

10. A surgical retractor according to claim 9 further including means on each of said wing members for receiving a retention pin.

11. A surgical retractor according to claim 10, wherein each of said wing members has a major portion adjacent said hinge extending from a first end adjacent said handle supporting end to a second end adjacent said hinge free end and a plurality of fingers depending from said second end and positioned on the opposite side of said wing members from said means for receiving a retention pin.

12. A surgical retractor according to claim 11, wherein said fingers are disposed at substantially right angles to said major portion.

13. A surgical retractor according to claim 8 further including a guide member mounted on said hinge free end.

14. A surgical retractor according to claim 13, wherein said guide member is disposed at substantially right angles to said hinge and tapers from a wide end at said hinge to a narrower free end.

15. A surgical retractor comprising:
   (a) a handle having a gripping end and an attachment end;
   (b) a hinge extending from said attachment end to a free end;
   (c) a pair of wing members mounted on said hinge for rotation relative to said hinge and angular rotation relative to each other, each of said wing members having a first side and a second side and having a first end adjacent said handle and a second end remote from said handle and each having a flange member extending from said first side at said second end; and
   (d) a guide member attached to said hinge free end.

16. A surgical retractor according to claim 15 wherein said guide member is disposed at substantially right angles to said hinge and extends to a tapered end terminating in a tip.

17. A surgical retractor according to claim 15 wherein said hinge has a longitudinal passageway extending therethrough.

18. A surgical retractor according to claim 17 further including a retention member on said second side of each of said wing members.

19. A surgical retractor according to claim 18 wherein each of said retention members has a passageway substantially parallel with said hinge passageway.

20. A surgical retractor according to claim 15 wherein each of said flange members has a plurality of fingers.

21. A surgical retractor according to claim 15 wherein each of said wing members has a substantially flat portion and each of said flange members is substantially perpendicular to its respective flat portion.

22. A surgical retractor according to claim 21 wherein each of said flange members forms a line of juncture with its respective flat portion and each of said lines of juncture form an obtuse included angle with said hinge.

23. A method of performing hip surgery comprising the steps of
   (1) providing a surgical retractor having
      (a) a handle having a gripping end and an attachment end;
      (b) a pivot pin extending along an axis from said attachment end to a free end;
      (c) a pair of wing members mounted on said pivot pin for rotation about said axis and rotation relative to each other;
   (2) incising the minimos muscle in line with its fibers;
   (3) inserting said retractor into the incision formed in said minimos muscle with said wing members folded to a retracted position and moving said retractor to a position at which opening of said wing members will expose the site of the hip intended for surgery;
   (4) opening said wings to expose said site; and
   (5) performing surgery at said site.

24. A method of performing hip surgery comprising the steps of:
   (1) providing a surgical retractor having
      (a) a handle having a gripping end and an attachment end;
      (b) a pivot pin extending along an axis from said attachment end to a free end, said pivot pin having a passageway extending along said axis;
      (c) a pair of wing members mounted on said pivot pin for rotation about said axis and rotation relative to each other; and
      (d) a guide member attached to said pivot pin free end and extending laterally of said axis;
   (2) incising the minimos muscle in line with its fibers;
   (3) inserting said retractor into the incision formed in said minimos muscle with said wing members folded to a retracted position and moving said retractor to a position at which said guide member is positioned to protect the neurovascular bundle and the opening of said wing members will expose the site of the hip intended for surgery;
   (4) inserting a retention pin through said pivot pin passageway and anchoring said retention pin into the hip bone;
   (5) opening said wings to expose said site; and
   (6) performing surgery at said site.

25. A method of performing hip surgery according to claim 24 further including the step of anchoring at least one of said wings in a fixed position following said step of opening.

26. A method of performing hip surgery according to claim 24 further including the step of anchoring said wings in a fixed position following said step of opening.

27. A surgical retractor comprising:
   (a) a handle extending from a first gripping section to a curved intermediate section to a supporting section, each of said sections having edges and a centerline defined by midpoints between said edges, said midpoints of said sections defining a common plane;
   (b) a hinge lying in said plane supported from said supporting section and extending to a free end; and
   (c) a pair of wing members mounted on said hinge for pivotal movement thereabout and angular movement relative to one another, each of said wing members having a major portion adjacent said hinge extending from a proximal end adjacent said supporting section to a distal end adjacent said free end.

28. The surgical retractor of claim 27 further including a flange member depending from said distal end at an angle to said major portion.

29. The surgical retractor of claim 27 further including a plurality of fingers depending from said distal end at an angle to said major portion.

30. The surgical retractor of claim 29, wherein said fingers are disposed at substantially right angles to said major portion.

31. The surgical retractor according to claim 27 wherein said hinge has a passageway extending therethrough for receiving a retention pin.

32. The surgical retractor of claim 31 further including means on each of said wing members for receiving a retention pin.

33. The surgical retractor according to claim 27 further including a guide member mounted on said hinge free end.

34. The surgical retractor according to claim 33, wherein said guide member is disposed at substantially right angles to said hinge and tapers from a wide end at said hinge to a narrower free end.

35. The surgical retractor according to claim 34 wherein said guide member extends in a direction reverse to the direction of said handle planar end portion.

* * * * *